(12) United States Patent
Studer (10) Patent No.: US 10,413,447 B2
(45) Date of Patent: Sep. 17, 2019

(54) OPHTHALMOLOGICAL PATIENT INTERFACE

(71) Applicant: Ziemer Ophthalmic Systems AG, Port (CH)

(72) Inventor: Thomas Studer, Neuchâtel (CH)

(73) Assignee: Ziemer Ophthalmic Systems AG, Port (CH)

( * ) Notice: Subject to any disclaimer, the term of this patent is extended or adjusted under 35 U.S.C. 154(b) by 72 days.

(21) Appl. No.: 15/629,150

(22) Filed: Jun. 21, 2017

(65) Prior Publication Data

US 2017/0367880 A1    Dec. 28, 2017

(30) Foreign Application Priority Data

Jun. 22, 2016    (EP) ..................................... 16175700

(51) Int. Cl.
     *A61F 9/009*      (2006.01)
     *A61B 3/00*      (2006.01)
     *A61F 9/008*      (2006.01)

(52) U.S. Cl.
     CPC ............ *A61F 9/009* (2013.01); *A61B 3/0083* (2013.01); *A61F 9/00825* (2013.01)

(58) Field of Classification Search
     CPC .......... A61F 9/009; A61F 9/008; A61F 9/007; A61B 3/0083
     See application file for complete search history.

(56) References Cited

U.S. PATENT DOCUMENTS

| 5,496,339 | A | * | 3/1996 | Koepnick | ............... | A61F 9/013 606/166 |
| 5,941,873 | A | * | 8/1999 | Korenfeld | .......... | A61B 17/0231 604/313 |
| 6,344,040 | B1 | * | 2/2002 | Juhasz | ................ | A61F 9/00827 606/4 |

(Continued)

FOREIGN PATENT DOCUMENTS

| EP | 0608052 A2 | 7/1994 |
| EP | 1731120 A1 | 12/2006 |

(Continued)

OTHER PUBLICATIONS

Jun. 22, 2016—(EP) App 16175700—Foreign Priority.
Dec. 23, 2016—(EP) Search Report—App 16175700.0.

*Primary Examiner* — Michael W Kahelin
*Assistant Examiner* — Sana Sahand
(74) *Attorney, Agent, or Firm* — Banner & Witcoff, Ltd.

(57) ABSTRACT

Disclosed is a patient interface for affixment on onto a patient eye, said patient interface including:
     a negative-pressure cavity designed for fluidic coupling to the patient eye;
     a first negative pressure interface with a first negative pressure aperture for fluidically coupling the negative-pressure cavity to a negative-pressure device to charge the negative pressure cavity with a negative pressure;
     a second negative pressure interface with a second negative pressure aperture for fluidically coupling the negative-pressure cavity to the negative-pressure device to charge the negative cavity with a negative pressure;
wherein the first negative pressure aperture and the second negative pressure aperture are arranged in a wall of the negative pressure cavity separate from and in close vicinity to each other.

20 Claims, 3 Drawing Sheets

(56) References Cited

U.S. PATENT DOCUMENTS

| | | | | |
|---|---|---|---|---|
| 8,623,001 | B2* | 1/2014 | Preuss | A61F 9/00827 606/107 |
| 2010/0274228 | A1* | 10/2010 | Mrochen | A61F 9/009 604/541 |
| 2011/0009851 | A1* | 1/2011 | Donitzky | A61F 9/00825 606/4 |
| 2011/0022035 | A1* | 1/2011 | Porter | A61F 9/00825 606/4 |
| 2012/0191077 | A1* | 7/2012 | Mrochen | A61F 9/009 606/4 |
| 2014/0128821 | A1* | 5/2014 | Gooding | A61M 1/0052 604/290 |
| 2014/0216468 | A1* | 8/2014 | Goldshleger | A61F 9/009 128/845 |
| 2014/0364744 | A1* | 12/2014 | Wellhoefer | A61F 9/00825 600/476 |
| 2015/0088103 | A1* | 3/2015 | Rathjen | A61F 9/009 606/4 |
| 2016/0296310 | A1* | 10/2016 | Jacoby | A61C 17/0208 |
| 2016/0331586 | A1* | 11/2016 | Deisinger | A61F 9/009 |

FOREIGN PATENT DOCUMENTS

| | | | | |
|---|---|---|---|---|
| EP | 2853247 | A1 | 4/2015 | |
| WO | 9304642 | | 3/1993 | |
| WO | WO 0041660 | A1 * | 7/2000 | A61F 9/013 |
| WO | 2012031277 | A1 | 3/2012 | |
| WO | 2015017343 | A1 | 2/2015 | |

* cited by examiner

OPHTHALMOLOGICAL PATIENT INTERFACE

This application claims priority to and the benefit of European Patent Application No. 16175700.0 filed on Jan. 22, 2016. The above-identified application is incorporated by reference herein in its entirety.

TECHNICAL FIELD

The present invention relates to devices and methods in the field of ophthalmology. The invention relates, in particular, to patient interfaces for coupling an application head to a patient's eye. The invention furthermore relates to a negative pressure devices and methods for coupling a patient interface onto a patient eye.

PRIOR ART

The use of radiation generators, in particular lasers, is known for the purposes of treating and/or diagnosing eye tissue. Corresponding devices such as ophthalmological laser apparatuses have, for example, a base device with a laser light source for generating laser pulses, for example femtosecond laser pulses, and an application head with a projection lens which is coupled to the patient eye for treatment purposes. The application head can be movably connected to the base device, for example by way of an articulated arm, wherein the articulated arm may simultaneously serve for optical beam guidance from the laser light source to the application head. By way of example, a corresponding arrangement is disclosed in EP 1731120. Moreover, there are devices in which the application head is integrated into the base instrument or in which other device arrangements are provided.

Mechanical and optical coupling of the application head to the patient eye, for example to the cornea and/or sclera of the patient eye, is carried out by way of a patient interface, wherein the patient interface may comprise a transparent contact body, through which the laser pulses emerging from the projection lens are guided and which, by way of the mechanical contact with the cornea, fixes the latter in respect of the patient interface and the projection lens. As an alternative to coupling by means of a contact body, provision can be made of liquid coupling, wherein a coupling liquid, for example a physiological saline solution, is situated between the cornea and the projection lens. By way of example, corresponding patient interfaces are known from WO 2012031277 or EP 2853247. The patient interface can be coupled to the patient eye by means of a vacuum and a negative-pressure cavity of the patient interface. The negative-pressure cavity is typically a suction ring placed onto the cornea. Most suction rings have two sealing lips. The lips can be attached to the sclera, the sclera and the cornea, or only the cornea. Furthermore, there are variants which only have one ring and which generate a vacuum over the whole eye, or variants which consist of a plurality of suction chambers/suction cups. The suction ring is the most common method of fastening, but there are also other known solutions. In any case, coupling to the patient eye is carried out by a vacuum or a negative pressure in a negative-pressure cavity of the patient interface, wherein the negative-pressure cavity, along the circumference thereof, abuts on the patient eye in a sealing manner and thereby couples to the patient eye in a fluidically sealing manner and seals the latter from the surroundings. The negative pressure can be generated by a negative-pressure generator, in particular a vacuum pump or a negative-pressure pump. In the known systems, the patient interface is coupled to the application head by means of e.g. a screw-in connection, bayonet closures or vacuum couplings.

SUMMARY OF THE INVENTION

During the application, it is necessary to ensure that the patient interface is connected to the patient eye in a secure and defined manner, and affixed on the latter. An insecure or detaching fixation would have as a consequence that the diagnostic or therapeutic beams emanating from the application head are no longer incident on the patient eye or—in a worst-case scenario—are incident on the patient eye in an undefined or unintended manner.

Such a situation may occur if the line connecting the negative-pressure cavity of the patient interface with the negative-pressure generator is blocked. By way of example, this can arise by virtue of the air flow directed out of the negative-pressure cavity sucking in liquid, e.g. viscoelastics used in cataract operations, sterile covering film or binding tissue (i.e. conjunctiva) when establishing the negative pressure and thus wholly or partly blocking the negative-pressure connection line itself, serving for aspiration, and/or the connector thereof to the negative-pressure cavity, e.g. the interior of the suction ring. In this case, a negative pressure may be established in a fluidic connection line that couples the negative pressure cavity with a negative pressure generator. In the negative pressure cavity itself, there may be no negative pressure or a negative pressure that is not sufficient for establishing or maintaining a secure fixation. Such a state, in which there appears to be a sufficient negative pressure or a vacuum in the negative-pressure cavity, but it is not in fact present, is also referred to as a pseudo-vacuum.

In particular, a blocking of the negative pressure connection by binding tissue is a serious issue for elderly patients where the tissue is comparatively flabby. To overcome this problem, it has been proposed to arrange a number of suction openings that are distributed symmetrically around the circumference of a suction ring. Such arrangement is disclosed, e. g. in U.S. Pat. No. 5,496,339. The rationale for such design is the assumption that, if a number of two or more negative pressure connections are present at different locations, not all of them will be blocked, e. g. by binding tissue.

Experience shows, however, that undesired material, in particular binding tissue, is likely to block all connections.

It is an overall objective to improve the situation regarding the generation and maintaining of negative pressure inside the negative pressure cavity of a patient interface. In a general way, the overall objective is achieved by the subject matter of the independent claims. Exemplary and/or particularly favorable embodiments are defined by the subject matter of the dependent claims.

According to a first aspect, the overall objective is achieved by a patient interface for affixment on onto a patient eye. The patient interface includes a negative-pressure cavity designed for fluidic coupling to the patient eye. The patient interface further includes a first negative pressure interface with a first negative pressure aperture for fluidically coupling the negative pressure cavity to a negative pressure device to charge the negative-pressure cavity with a negative pressure. The patient interface further includes a second negative pressure interface with a second negative pressure aperture for fluidically coupling the negative-pressure cavity to the negative-pressure device to charge the negative-pressure cavity with a negative pressure.

The first negative pressure aperture and the second negative pressure aperture are arranged in a in a wall of the negative pressure cavity separate from and in close vicinity to each other.

Affixing the patient interface on the patient eye means an affixment of a patient interface body on patient eye tissue, typically on the cornea and/or sclera. A side of the patient interface lying opposite the patient eye is designed for coupling an ophthalmologic application head. The patient interface as a whole can comprise further components such as, in particular, connection lines, in particular negative pressure supply lines that extend from a patient interface body. The patient interface body particularly includes the negative pressure cavity with first and second negative pressure interface.

The first and second negative pressure aperture are openings in a wall of the negative pressure cavity via which air that is initially present inside the negative pressure cavity may be suck out of the negative pressure cavity, thereby charging the negative pressure cavity with a negative pressure, respectively under pressure as compared to the environmental atmospheric pressure.

The first negative pressure aperture and the second negative pressure aperture being arranged separate from each other means that they are distinct from each other and separated from each other by material of the wall in which they are arranged.

At least a portion of the fluidic flow paths form the negative pressure apertures towards a negative pressure device or negative pressure generator is also fluidic separates.

In a fluidic context, separate means in particular that there is no fluidic connection and separate flow channels respectively lumen are provided. A mechanical integration, e. g. via tubings with separate lumen and/or fluidic multiple connectors, in particular double connectors, is not precluded.

The arrangement of two separate negative pressure apertures in close vicinity to each other is surprisingly found to result in material such as pieces of sterile foil and in particular binding tissue that may clog or occlude the negative pressure coupling, is, if present, suck into only one of the negative pressure apertures and negative pressure interfaces, with the other remaining open respectively through-going. While being counter-intuitive, such arrangement is found to be advantageous over an arrangement with negative pressure apertures that are remote, e. g. diametric to each other. In close proximity of the apertures a metastable behavior can be observed when vacuum is applied to both apertures: slight deviation from symmetry (which are always present in the potentially obstructing material but also in the patient interface) lead to a preference for the obstructing material, in particular the binding tissue (conjunctiva), to be sucked towards or even into one of the apertures. Sucking tissue towards or even into one aperture stretches the tissue above the other aperture. This automatically prevents closure of the second aperture.

In a variant, more than two negative pressure interfaces, for example a third negative pressure interface with a third negative pressure aperture and also a fourth negative pressure interface with a fourth negative pressure aperture may be provided.

Apart from the providing a first and second negative pressure interface in accordance with the present disclosure, the patient interface can be embodied in a design known per se and in a single part or multipart manner. By way of example, the negative-pressure cavity is formed as a suction ring by a chamber which is open toward the patient eye and encircles the latter in a ring-shaped manner.

Exemplary multipart patient interfaces have a design in accordance with US20150088103A1 and EP2853247A1 which, in respect of the design of exemplary patient interfaces, are incorporated into the present document, also for exemplary embodiments described in more detail below. However, the specific structure of the patient interface is not mandatory.

Typically, the patient interface is configured as a disposable product for economic reasons and as a result of safety considerations and it is preferably packaged in a sterile manner at first. However, in principle, the patient interface can also be designed entirely in parts for multiple use.

In an embodiment, the first negative pressure aperture and the second negative pressure aperture are arranged in a curved surface, in particular of a circumferential wall of the negative-pressure cavity. For the case of the negative pressure reservoir being a suction ring, a circumferential wall has the shape of an (approximated) cylinder surface. An arrangement in a curved surface is particularly favorable for preventing material, in particular binding tissue, into both the first and second negative pressure aperture.

The curvature respectively diameter of the surface respectively wall is determined by the design and dimensions of the patient interface and in particular the negative pressure cavity. For a negative pressure cavity with a suction ring, the first and second negative pressure aperture may be arranged in an outer wall with a diameter in a typical range of 16-24 millimeters.

In an alternative embodiment, the first negative pressure aperture and the second negative pressure aperture are arranged in a top wall of the negative-pressure cavity.

In an embodiment, a separation element is arranged inside the negative-pressure cavity and between the first and second negative-pressure aperture. A separation element may, e. g. in form of a ridge, further prevent material, in particular binding tissue, to be undesirably suck into both negative pressure apertures.

In an embodiment, an angular distance between the first and second negative pressure aperture does not exceed 30 degrees and/or a distance between the first and second negative pressure aperture does not exceed 5 millimeters. In a particular embodiment, the angular distance between the first and second negative pressure aperture does not exceed 20 degrees and/or a distance between the first and second negative pressure aperture does not exceed 3 millimeters.

In an embodiment, the first negative pressure interface and the second negative pressure interface are designed for separate fluidic coupling with the negative-pressure device. For this type of embodiment, completely separate flow paths are provided between the first respectively second negative pressure aperture and the negative pressure device via separate lumen. Such arrangement is favorable under a redundancy point of view.

Alternatively, the flow paths merge directly in the patient interface or between the patient interface and a negative pressure device, for example via a split negative pressure connection line. In a variant, the flow paths directly merge directly in the patient interface respectively patient interface body, e. g. via an injection-molded negative pressure distribution structure that branches a common negative pressure lumen that branches into a first negative pressure lumen and a second negative pressure lumen, with the first negative pressure lumen opening into the first negative pressure aperture and the second negative pressure lumen opening into the second negative pressure aperture. In such embodiment, the first negative pressure interface and the second negative pressure interface are realized in a partly integral, with the common negative pressure lumen belonging to both the first and second negative pressure interface.

In an embodiment, the first negative-pressure interface includes first connection nozzle and the second negative-pressure interface includes a second connection nozzle. The connection nozzles are designed for a fluid tight connection with a corresponding negative pressure connection line, e. g. tubing, in a generally known way, for example via adhesive bonding, ultrasonic welding, gluing, or simply via press fitting, employing the elastic material properties of the tubing. In embodiments with a common negative pressure lumen as explained before, only a single connection nozzle may be present. The connection nozzle or connection nozzles may be formed integral with the patient interface body, for example by injection molding.

In an embodiment, the patient interface includes a pressure sensor interface for fluidically coupling the negative-pressure cavity to a fluidic pressure sensor. The interface-side pressure sensor interface is functionally separate from the first and second negative pressure interface that are used for establishing and maintaining the negative pressure in the negative pressure cavity 20.

In an embodiment, the negative-pressure cavity is ring-shaped and arranged circumferentially around an axially through-going central room. In application, laser radiation passes through the central room from the application head to the patient's eye.

According to a further aspect, the overall objective is achieved by an ophthalmologic arrangement. The ophthalmologic arrangement includes a patient interface according to any embodiment as explained before and/or further below. The ophthalmologic arrangement further includes a negative pressure device, the negative pressure device including a negative pressure generator in fluidic coupling with the first and second negative pressure interface.

The negative-pressure generator typically includes a vacuum pump with a design known per se, but it can additionally or alternatively also comprise other suction or aspiration devices, in particular a negative-pressure reservoir in the form of a container to which negative pressure is applied. Optionally, the negative-pressure device includes further fluidic components, such as one or more valves, some or all of which are operatively coupled to the control unit and can be controlled by the latter, chokes or positive-pressure valves, and may further include one or more sensors, such as pressure sensors and/or gas flow sensors, fluidic connectors, and/or moisture separators, e. g. drip chambers.

In an embodiment, the negative pressure device includes a first valve unit and a second valve unit. The first valve unit is, in an operational state, fluidic coupled with the first negative pressure interface while the second valve unit is separately coupled with the second negative pressure interface. The first and second valve unit can serve, in particular, for switching between different modes of operation or operating states of the negative-pressure device, for example for switching between an aspiration operation for building up negative pressure in the negative-pressure cavity independently via the first and second negative pressure interface, a holding operation or stationary operation for maintaining the desired negative pressure, and a ventilation operation, in which the negative-pressure cavity is ventilated in respect to the surroundings and the affixment of the patient interface on the patient eye is lifted.

Typically, the negative pressure device includes a control unit. The control unit is realized as an electronic circuit in a manner known per se and typically includes one or more microprocessors and/or microcontrollers, memory components, other analog and/or digital semiconductor components, etc. Methods and algorithms for controlling the negative-pressure generator and for evaluating and processing the pressure sensor signal are typically realized wholly or in part in the form of program code for the at least one microprocessor and/or microcontroller, but can also be realized wholly or in part by corresponding circuit components.

The patient interface can be designed for coupling to the patient eye by means of coupling liquid and/or for applanation-type coupling by means of a transparent contact body. In the case of liquid coupling, the setpoint negative, which is required for secure affixment of the patient interface and which should be built up and maintained by the negative-pressure device, lies in a typical range of −200 mbar . . . −800 mbar, for example, wherein a higher negative pressure is typically selected for coupling an applanation-type patient interface than for a patient interface with liquid coupling. In this document, negative pressures denote negative pressures in relation to ambient atmospheric pressure. In stationary operation after the negative pressure has been built up in the negative-pressure cavity, the control unit and the negative-pressure generator are typically designed to compensate pressure variations and maintain the setpoint negative pressure. The patient interface can be coupled to a therapeutic or diagnostic apparatus, for example a laser application head, before or after it is coupled to the patient eye.

In typical embodiments, the control unit is functionally coupled to an alarm device or designed for functional coupling to an alarm device. The control unit then is furthermore designed to activate the alarm device in the case of a detected faulty fluidic coupling of the negative-pressure cavity. The alarm device can be a component of the negative-pressure device and/or be external therefrom. The alarm device can typically comprise acoustic transducers such as loudspeakers, buzzers or sirens, in addition to optionally required actuation circuits such as warning lamps, light-emitting diodes etc., in addition to optionally present actuation circuits.

Furthermore, the control unit can be designed for operative wired and/or wireless coupling to a diagnostic and/or therapeutic radiation generator, in particular an ophthalmological laser device. The control unit can furthermore be configured to deactivate or switch off the radiation generator in the case of a detected faulty fluidic coupling of the negative-pressure cavity.

In an embodiment, the ophthalmologic arrangement is in separate fluidic coupling with the first and second negative pressure interface. For this type of embodiment, the negative pressure device includes a first negative pressure coupler and a fluidic separate second negative pressure coupler are provided, being it as separate couplers or as a double coupler with separate flow channels. In variants where the patient interface includes a common negative pressure lumen as explained before, only a single negative pressure connector may be present.

In an embodiment, the ophthalmologic arrangement is configured to charge the negative-pressure cavity with a negative pressure via the first negative pressure interface only in a first step and to additionally charge the negative-pressure cavity with the negative pressure via the second negative pressure interface subsequently. For this type of embodiment, any undesired material, in particular binding tissue, is suck into the first negative pressure aperture, while the negative pressure aperture stays open.

In an embodiment, the negative pressure device is configured to determine correct establishment of a negative pressure via the first negative pressure interface and to additionally charge the negative-pressure cavity with the negative pressure via the second negative pressure interface in the affirmative case only. This type of embodiment requires a fluidic separate coupling of the first and second negative pressure interface with the negative pressure device. Determining whether the negative pressure is achieved may be determined by a pressure sensor of the negative pressure device in fluidic coupling with the first negative pressure interface (via the first negative pressure connection line, or via a pressure sensor that is coupled with the negative pressure cavity via a separate pressure sensor interface, according to an embodiment as explained before. Correct establishment of the negative pressure may be determined via a pressure sensor. In an alternative, correct establishment of the negative pressure via the first negative pressure interface is not determined with a sensor, in particular a pressure sensor, but the negative pressure cavity is charged with the negative pressure via the second negative pressure interface with a delay time after beginning charging the negative pressure cavity with the negative pressure via the first negative pressure interface.

According to a still further aspect, the overall objective is achieved by a method for affixing a patient interface on a patient eye. The method includes charging a negative pressure cavity of the patient interface with negative pressure via a first negative pressure interface and charging the negative pressure cavity via a second negative pressure interface. A first negative pressure aperture of the first negative pressure interface and a second negative pressure aperture of the second negative pressure interface are arranged in a in a wall of the negative pressure cavity separate from and in close vicinity to each other.

In an embodiment, the method includes charging the negative-pressure cavity with a negative pressure via the first negative pressure interface only in a first step and to additionally charging the negative-pressure cavity with the negative pressure via the second negative pressure interface subsequently.

Methods in accordance with the present disclosure may be carried out using devices, in particular patient interfaces, negative pressure devices and ophthalmologic arrangements in accordance with the present disclosure. Therefore, embodiments of devices as disclosed in this documents disclose, at the same time corresponding method embodiments that may be carried out with the corresponding devices, and vice versa.

EXEMPLARY EMBODIMENTS

Exemplary embodiments are presented below with additional reference to the figures.

Figure 1A:
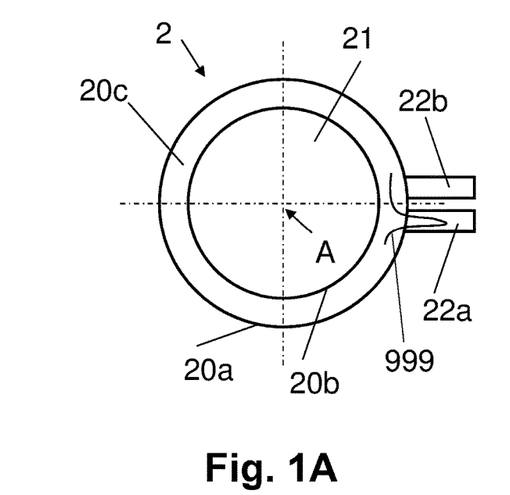
FIG. 1A, 1B schematically shows an embodiment of a patient interface in a bottom view and a side view.
Figure 1B:
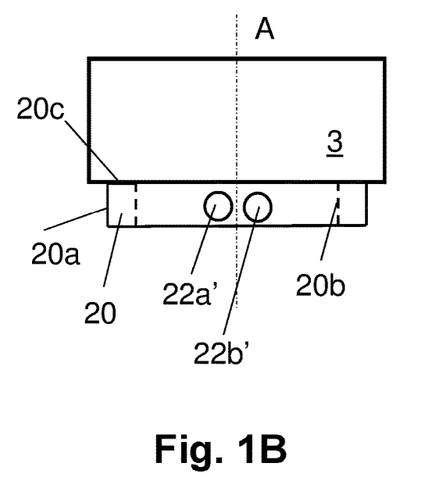

Reference is first made to FIG. 1A, 1B. In FIG. 1A, 1B, reference sign 2 denotes a patient interface in accordance with the present disclosure in a schematic view. FIG. 1A shows the patient interface 2 in schematic bottom view (from the patient's eye). FIG. 1B shows the patient interface 2 in a schematic side view and in operational coupling with an ophthalmologic application head 3.

The patient interface 2 includes a suction ring of U-shaped cross section, with an outer wall 20a and an inner wall 20b as circumferential walls in concentric arrangement around an axially through-going central room 21. The central room 21 is exemplary rotational symmetric around axis A with a circular footprint and exemplary of cylindrical shape. In a typical embodiment, the outer diameter of the suction ring is about 20 millimeters. Alternatively, the central room may have an elliptical footprint with the height of the central room 21 corresponding to the height of the outer wall 20a and inner wall 20b. In a variant, the inner wall 21b is realized respectively replaced by a sealing lip of negligible or low height. Together with a ring-shaped top wall 20c the outer wall 20a and the inner wall 20b delimit a negative pressure cavity 20. In the application state, outer wall 20a is placed on and abuts the sclera of the patient eye (not depicted here), while the inner wall 20b is placed on and abuts the limubs. In an alternative arrangement, both the outer wall 20a and the inner wall 20b are placed on and abut the sclera. Further variants contacting partially or entirely the cornea are possible as well. Further in the application state, the central room 21 is situated between the corneal surface of the patient eye and the application head 3 such that the cylinder room 21 is delimited by the inner wall 20b as cylinder shell, the cornea as bottom surface an element of the application head 3 as top surface. The central room 21 can favorably be filled with e.g. physiological saline solution as a coupling liquid. For affixing the patient interface 2 or the patient interface 2 to the patient eye, a negative pressure or vacuum is generated in the negative-pressure cavity 20 and a negative pressure or vacuum thus fixes the patient interface 2 on the patient eye.

The patient interface 2 further includes a first negative pressure interface 22a and a second negative pressure interface 22b for applying the negative pressure. The first and second negative pressure interface, 22a, 22b are exemplary shown as elongated hollow connection nozzles in a side-by-side arrangement that open into the negative pressure cavity via corresponding first and second negative pressure apertures, 22a', 22b' in the outer wall 20a. The nozzles 22a, 22b are designed for coupling with a negative pressure device via a corresponding negative pressure supply lines (tubing) as generally known in the art.

The first negative pressure aperture 22a' and the second negative pressure aperture 22b' are separate from each other. Consequently, either of the first negative pressure aperture 22a' or the second negative pressure aperture 22b' being clogged or occluded does not affect the other of the first and second negative pressure aperture. Favorably, the first and second negative pressure aperture are arranged side-by-side and in a common height, in particular distance from the lower edge of the outer wall, 20a.

While being separate from each other, the first and second negative pressure aperture, 22a', 22b' are located in as close vicinity to each other as possible, on accordance with the overall design. Surprisingly, pieces of sterile covering film, binding tissue (reference sign 999) or other elements or particles that may be present inside the negative-pressure cavity when applying negative pressure, tend to be suck into and accordingly occlude only one of the first and second negative pressure apertures, 22a', 22b', but not both of them, provided that they are sufficiently close to each other, resulting from the meta stable behavior as explained above in the general description.

The dimensioning of the negative pressure cavity 21, first and second negative pressure interface 22a, 22b and the negative pressure that is applied, is favorably such that one of the first and second negative pressure interfaces 22a, 22, respectively negative pressure apertures, 22a', 22b', is sufficient for affixing the patient interface 2 on the patient's eye.

In the shown embodiment of FIG. 1A, 1B, the first and second connection nozzle 22a, 22b extend parallel to each other thereby allowing simple coupling with a double-lumen tube, thus providing functionally separate first and second negative pressure supply lines, which however, is not essential. Other arrangements and, e. g. two separate negative pressure supply lines, each with a single lumen, may be used as well. In a further variant, the connection are arranged radial rather than in parallel. In case of two separate tubes or a double-lumen tube, operatively coupling to a negative pressure device may be realized e. g. via separate fluidic connectors or a double connector with two separate flow channels.

Coupling the first and second negative pressure interface 22a, 22b via separate tubes respectively separate lumen is favorable in particular for redundancy purposes and in connection with a negative pressure device according to an embodiment as discussed further below. It is, however, in principle also possible to merge the first and second negative pressure interface outside the negative pressure cavity 20 and couple them with a negative pressure device via a common single lumen provided that an occlusion may occur in the separate nozzles respectively negative pressure interfaces, but not the common tubing.

Figure 2:
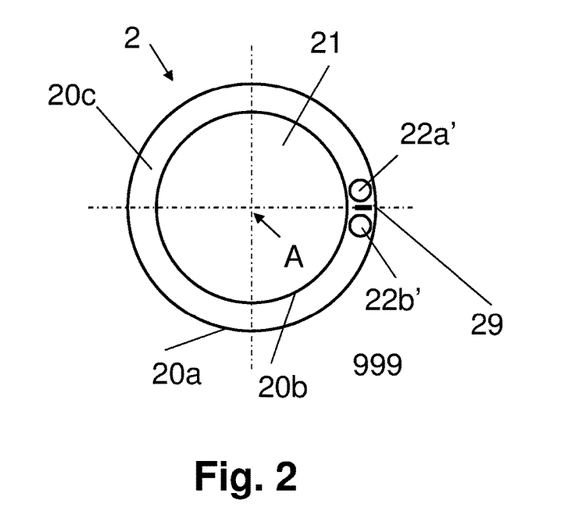
FIG. 2 schematically shows a further embodiment of a patient interface in a bottom view.

In the following, reference is additionally made to FIG. 2. FIG. 2 shows a further embodiment of the patient interface 2 in a schematic bottom view (similar to FIG. 1A). Since the overall design is similar to the embodiment of only differentiating aspects are discussed in the following.

In the embodiment of FIG. 2, the negative pressure apertures 22a, 22b are provided in the ring-shaped top wall 20c, rather than the outer wall 20a. Further, an optional separation element is arranged inside the negative pressure cavity 20. The separation element is embodied as radial ridge 29 between the first and second negative pressure aperture, 22a', 22b'. Despite the ridge 29, the negative pressure cavity 20 is favorably fluidic continuous, i. e. the ridge 29 does not divide the negative pressure cavity 20 into fluidic separate halves. The ridge 29 can also be applied in the embodiment of FIG. 1 when sufficiently away from the sealing edge in order not to reduce the contact pressure of the sealing lip.

It is noted that the geometry of the patient interface 2 is simplified and focused on aspects of particular relevance in the context of the present disclosure. For example, the outer wall 22a and the inner wall 22b may be angled with respect to each other rather than being parallel to each other and the symmetry axis A. If the inner wall 20b is non-parallel to the symmetry axis A, the central room 21 has the shape of a truncated cone rather than being cylindrical (see embodiment of FIG. 4). Further, the outer wall 22a and the inner wall 22b may be of different height. In particular, the outer wall 22a may be somewhat higher in view of the curved eye surface. Further, sealing elements, such as circumferential sealing lips that may be made from elastic material and formed in an integral way, e. g. by 2K injection molding, may be present. Further, the inner wall 20b may be replaced by a circumferential sealing lip of negligible respectively low height, in which case the cross sectional shape of the negative pressure cavity 20 is approximately triangular in an applied state. Further, the top wall 20c may smoothly run into the outer wall 20, resulting in the outer wall 20a and the top wall 20c being a common element with smooth surfaces.

Figure 3:
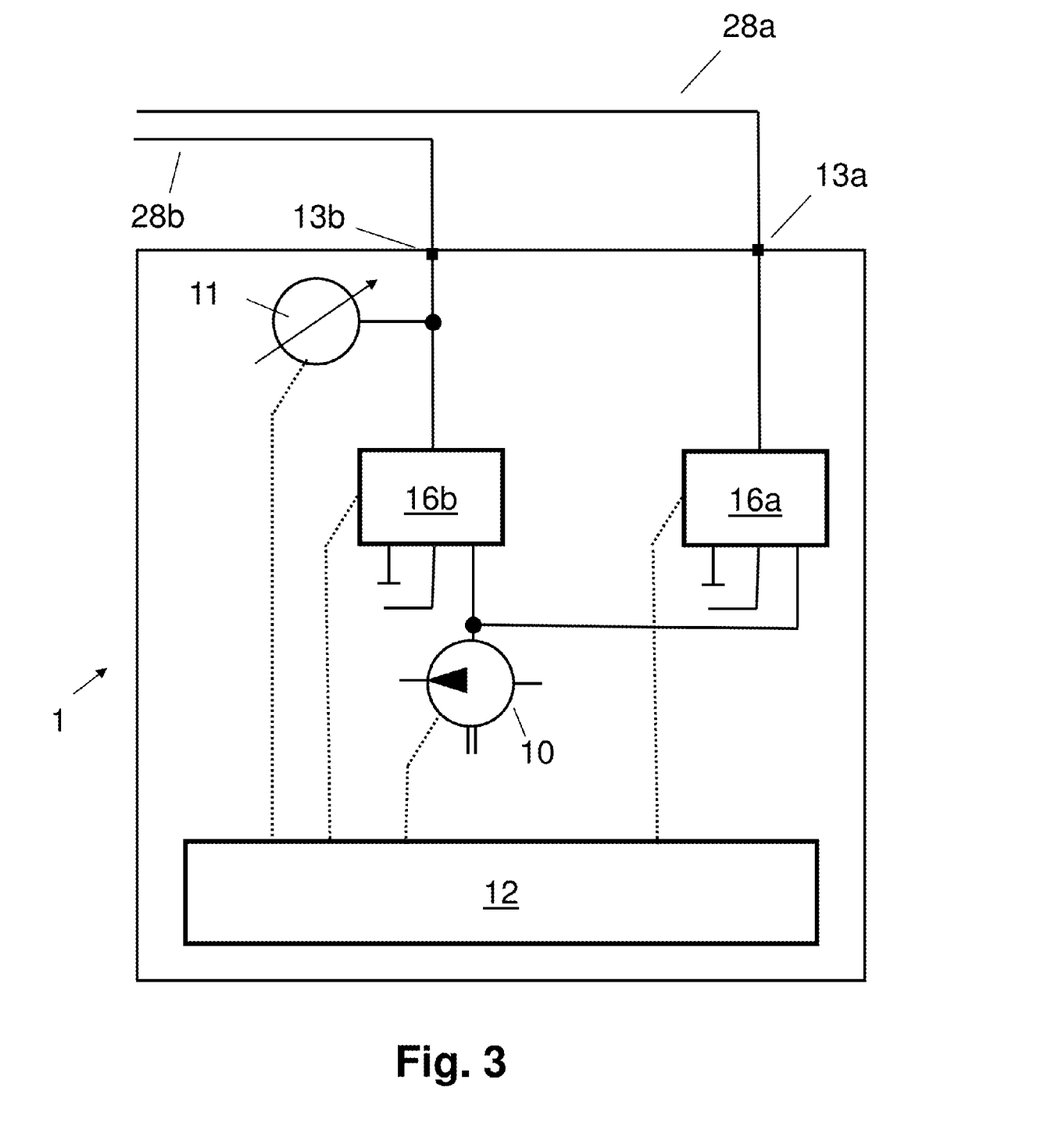
FIG. 3 schematically shows an embodiment of a negative pressure device in a functional view.

In the following, reference is additionally made to FIG. 3. In FIG. 3, reference sign 1 denotes a negative pressure device. A negative pressure device and a patient interface 2 in accordance with the present disclosure, e. g. a patient interface as shown in FIG. 1, 2, make, in combination, an ophthalmologic arrangement.

The negative-pressure device 1 includes a negative-pressure generator, which is exemplarily realized as by a vacuum pump 10. The negative-pressure device 1 furthermore includes a pressure sensor 11, a first valve unit 16a and a second valve unit 16b.

The negative pressure device 1 further includes a control unit 12 operatively connected to the negative-pressure generator 10, the pressure sensor 11, and the first and second valve unit 16a, 16b. The control unit 10 is typically formed by an electric/electronic circuit in a manner known per se. In particular, the control unit 12 can comprise one or more microprocessors and/or microcontrollers with appropriate program code for controlling the function of the negative-pressure device 1. The control unit 12 may comprise an alarm device or it is operatively coupled to an alarm device (not depicted here). An alarm is sounded by way of the e.g. optical and/or acoustic alarm device in the case of a lost, insufficient coupling of the patient interface 2 to the patient eye. The control unit 12 can furthermore be operatively coupled to a ophthalmological laser light source connected to the application head 3 or contained in the application head 3 or operatively coupled to any other beam generator and it can deactivate or switch off said ophthalmological laser light source or other beam generator in the case of a detected faulty fluidic coupling of the negative-pressure cavity.

The negative-pressure device 1 furthermore includes exemplarily a first fluidic negative pressure coupler 13a and a second fluidic negative pressure coupler 13b that are formed, for example, by detachable fluidic plug-in connectors or couplers, e.g. fluidic coupling sleeves, or a double plug-in connector with two separate flow channels via the first and second negative pressure coupler.

FIG. 3 further shows a negative pressure supply line 28a and a fluidic separate second negative pressure supply line 28b. In operation, the first negative connection line is fluidic coupled with the first negative pressure interface 22a and the second negative pressure supply line is fluidic coupled with the second negative pressure interface 22b as explained before.

The first and second negative pressure coupler 13a, 13b are each fluidic coupled with an associated first respectively second valve unit 16a, 16b. The pressure sensor 11 is also coupled with the first negative pressure coupler 13a to measure the (negative pressure) in the first negative pressure supply line 28.

The first valve unit 16a is configured to alternatively couple the first negative pressure coupler 13a with the negative pressure generator 10 or with the environment or to seal the fluidic connector 13a. Similarly, the second valve unit 16b is configured to alternatively couple the second negative pressure coupler 13b and the pressure sensor 11 with the negative pressure generator 10 or with the environment, or to seal the second negative pressure coupler 13b and the pressure sensor 11.

For the purposes of coupling the patient interface 2 onto the patient eye, the control unit 12 controls the first valve unit 16a to connect the first negative pressure coupler 13a with the negative pressure generator 10 and further controls the second valve unit 16b to fluidic isolate the second negative pressure coupler 13b.

Subsequently, the control unit 12 activates the negative pressure generator 10 such that the air originally present in the negative-pressure cavity 20 as well as in the first and second negative pressure supply line, 28a, 28b is at least partly aspirated, and the negative pressure cavity 20 is charged with negative pressure.

For a design of the patient interface 2 in accordance with the present disclosure, any particles, binding tissue or the like may be suck via the first negative pressure aperture 22a' and potentially into the first negative pressure interface 22a, as schematically shown in FIG. 1A for binding tissue (conjunctiva) 999.

Subsequently, after a delay time of e. g. 2 seconds, the control unit 12 controls the second valve unit 16b to connect the second negative pressure coupler 13b with the negative pressure generator 10, while maintaining the state of the first valve unit 16a. In this way, a negative pressure is generated in the negative pressure cavity 20 that fixes the patient interface 2 on the patient eye, even if the first negative pressure interface 22b is partly of fully occluded. Via the pressure sensor 11, the pressure inside the negativities pressure cavity 20 is supervised respectively monitored.

Subsequently, the control unit 12 switches the negative pressure device 1, in a manner known per se, into a stationary holing operation, in which the negative pressure in the negative-pressure cavity 20 is kept substantially constant by corresponding control of the valve units 16a, 16b and/or the negative pressure generator 10. This state is maintained until a pressure equalization with the surroundings is established deliberately and the patient interface 2 is thus detached from the cornea of the patient eye by controlling the first and second valve unit 16a, 16b to fluidically connect the first and second negative pressure coupler 13a, 13b, and accordingly the negative pressure cavity 20, with the environment. During operation, the pressure in the negative pressure cavity 20 is continuously monitored respectively supervised via pressure sensor 11.

Figure 4:
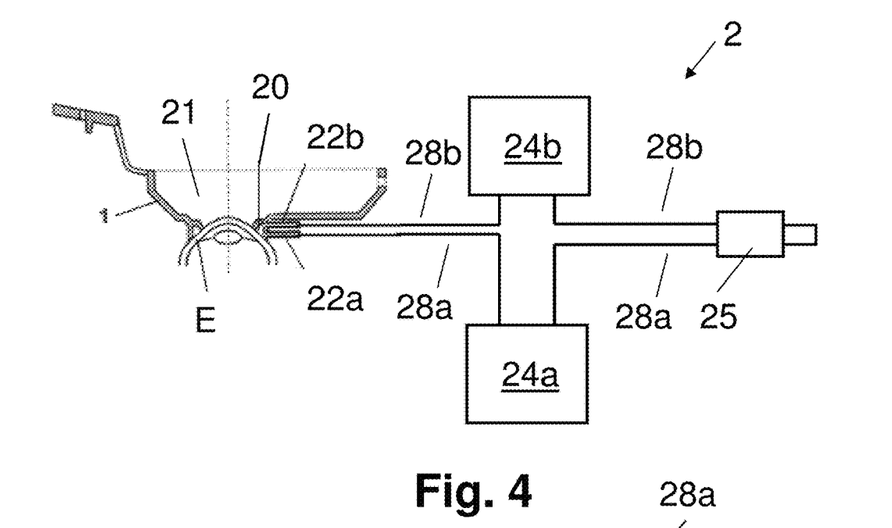
FIG. 4 schematically shows a further embodiment of a patient interface.

In the following, reference is additionally made to FIG. 4. FIG. 4 schematically depicts part of a patient interface 2 in accordance with an exemplary embodiment of the invention together with a patient eye E. The patient interface 2 has a patient interface body 2' with a ring-shaped negative-pressure cavity 20 and a central room 21, as explained above in the context of FIG. 1, FIG. 2. Two fluidic connection nozzles serve as first and second negative pressure interface 22a, 22b. It is noted that the nozzles are shown one above the other, but may also be in a side-by-side arrangement as in the before-described embodiments. With exception of the first and second negative pressure interface in accordance with the present disclosure, the patient interface body 2' may be realized in accordance with the disclosure of EP 2853247 A1. First and second negative pressure interface 22a, 22b are connected with a double connector 25 via the first and second negative connection line 28a, 28b.

The patient interface 2 of FIG. 4 furthermore includes a first drip chamber 24a and a second drip chamber 24b optionally seated in the first and second negative-pressure connection line 28a, 28b. The drip chambers separate liquid aspirated from the negative-pressure cavity 20, e.g. drops of physiological saline as a coupling liquid, and thus prevents these from reaching the fluidic components of the negative-pressure device 1 during operation.

The negative pressure device 1 may be altered or modified in a number of ways. For example, a first and a separate negative pressure generators may be provided. Similarly, a first and a separate second pressure sensor may be provided.

Further valves may be provided for additional functionality and to enable further fluidic configurations. Thus, for example, provision can be made for the negative-pressure generator to be connected fluidically to the surroundings. Furthermore, a negative-pressure reservoir with a volume of the order of e.g. one liter can be provided, said negative-pressure reservoir being connectable to the negative-pressure supply lines 28a, 28b and/or the negative-pressure generator 10 under control of the control unit 12. In particular, such a negative-pressure reservoir serves for fluidic buffering and can furthermore serve for aspirating small amounts of air, for example in the case of a relatively small and short-lived leakage of the negative-pressure cavity 20, in place of, and within principle the same function as, the negative-pressure generator 10. Advantageously, a negative pressure is built up in the optional negative-pressure reservoir by means of the negative-pressure generator 10.

Furthermore, a further pressure sensor may be provided that is coupled with the first negative pressure coupler 13a and the first valve unit 16a in the same way as the pressure sensor 11 is coupled with the second negative pressure coupler 13b and the second valve unit 16b. In this case, the pressure sensor 11 as shown in FIG. 3 is a second pressure sensor and the further pressure sensor is a first pressure sensor. Such arrangement is favorable for redundancy respectively safety purposes. Further, a first pressure sensor may be used to monitor the establishment of the negative pressure in the negative pressure cavity 20 in the initial phase as explained before.

Furthermore, the patient interface may comprise a functionally and in particular fluidic separate pressure sensor interface with a pressure sensor aperture that may be designed generally in the same way as the first and second negative pressure interface. The negative pressure device 1 may, in this case, include a further separate pressure sensor in operative coupling with the control unit and be arranged for separate fluidic coupling with the pressure sensor interface via a separate fluidic pressure sensor connection line.

Figure 5:
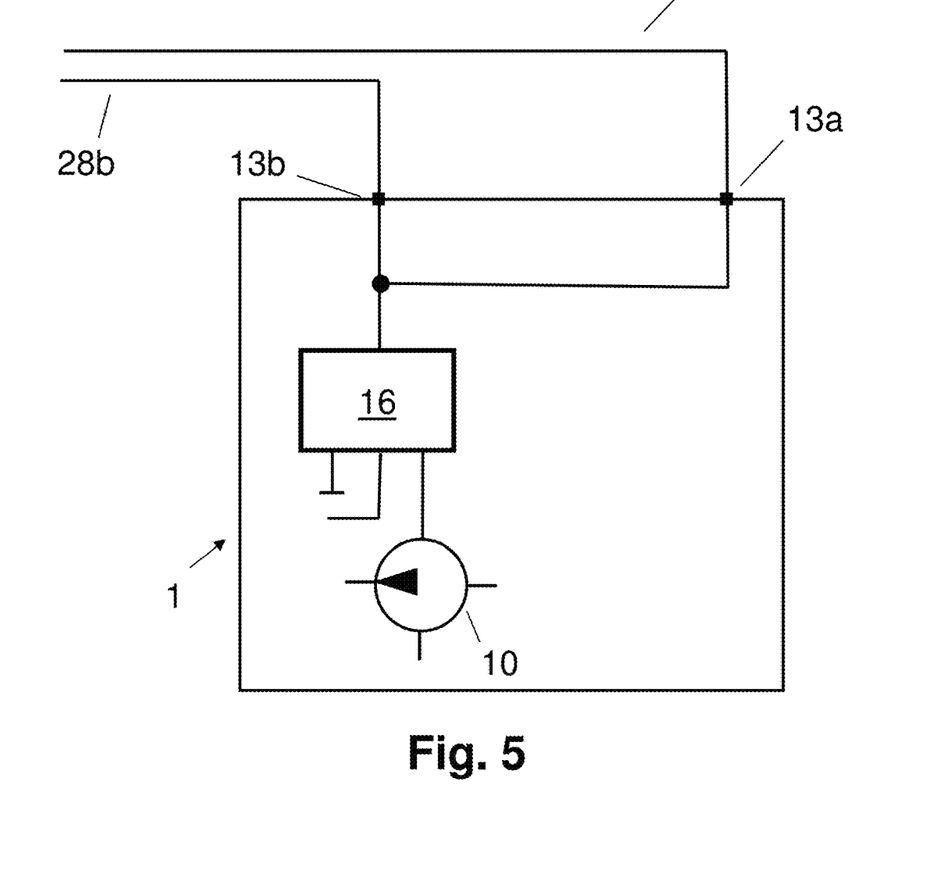
FIG. 5 schematically shows an embodiment of a negative pressure device in a functional view.

In the following, reference is additionally made to FIG. 5, showing a further exemplary embodiment of the negative pressure device 1 in a view similar to FIG. 3, with a reduced number of functional units and reduced complexity. In the embodiment of FIG. 5, the first negative pressure coupler 13a and the second negative pressure coupler 13b are both fluidic coupled with a common valve unit 16. The valve unit 16a is configured to alternatively couple both the first and second negative pressure coupler 13a, 13b alternatively with the negative pressure generator 10 or with the environment or to seal the both the first and second negative pressure coupler 13a, 13b. The first and second negative pressure coupler 13a, 13b may be structurally distinct or be designed to couple with a double connector 25 as shown in FIG. 4.

The invention claimed is:

1. A patient interface for affixment on a patient eye, the patient interface comprising:
   a negative pressure cavity designed for fluidic coupling to the patient eye;
   a first negative pressure interface with a first negative pressure aperture for fluidically coupling the negative pressure cavity to a negative pressure device to charge the negative pressure cavity with a negative pressure; and a second negative pressure interface with a second negative pressure aperture for fluidically coupling the negative pressure cavity to the negative pressure device to charge the negative pressure cavity with a negative pressure;

wherein the first negative pressure aperture and the second negative pressure aperture are arranged in a wall of the negative pressure cavity separate from and in close vicinity to each other, wherein the first negative pressure aperture and the second negative pressure aperture are arranged next to each other on the circumference of the negative pressure cavity, wherein at least one of:
an angular distance between the first negative pressure aperture and the second negative pressure aperture does not exceed 30 degrees, and
a distance between the first negative pressure aperture and the second negative pressure aperture does not exceed 5 millimeters.

2. The patient interface of claim 1, wherein the first negative pressure aperture and the second negative pressure aperture are arranged in a curved surface of a circumferential wall, of the negative pressure cavity.

3. The patient interface of claim 1, wherein the first negative pressure aperture and the second negative pressure aperture are arranged in a top wall of the negative pressure cavity.

4. The patient interface of claim 1, wherein a separation element is arranged inside the negative pressure cavity and between the first negative pressure aperture and the second negative pressure aperture.

5. The patient interface of claim 1, wherein the first negative pressure interface and the second negative pressure interface are designed for separate fluidic coupling with the negative pressure device.

6. The patient interface of claim 5, wherein the first negative pressure interface includes a first connection nozzle and the second negative pressure interface includes a second connection nozzle.

7. The patient interface of claim 1, including a pressure sensor interface for fluidically coupling the negative pressure cavity to a fluidic pressure sensor, wherein the pressure sensor interface is functionally separate from the first negative pressure interface and the second negative pressure interface.

8. The patient-interface of claim 1, wherein the negative pressure cavity is ring-shaped and arranged circumferentially around an axially through-going central room.

9. An ophthalmological system comprising:
a patient interface comprising:
a negative pressure cavity designed for fluidic coupling to the patient eye;
a first negative pressure interface with a first negative pressure aperture for fluidically coupling the negative pressure cavity to a negative pressure device to charge the negative pressure cavity with a negative pressure; and
a second negative pressure interface with a second negative pressure aperture for fluidically coupling the negative pressure cavity to the negative pressure device to charge the negative pressure cavity with a negative pressure;

wherein the first negative pressure aperture and the second negative pressure aperture are arranged in a wall of the negative pressure cavity separate from and in close vicinity to each other, wherein the first negative pressure aperture and the second negative pressure aperture are arranged next to each other on the circumference of the negative pressure cavity, wherein at least one of:
an angular distance between the first negative pressure aperture and the second negative pressure aperture does not exceed 30 degrees, and
a distance between the first negative pressure aperture and the second negative pressure aperture does not exceed 5 millimeters; and the negative pressure device, the negative pressure device comprising a negative pressure generator in fluidic coupling with the first negative pressure interface and the second negative pressure interface.

10. The ophthalmologic system of claim 9, wherein the negative pressure generator is in separate fluidic coupling with the first negative pressure interface and the second negative pressure interface.

11. The ophthalmologic system of claim 10, wherein the negative pressure device is configured to charge the negative pressure cavity with a negative pressure via the first negative pressure interface only in a first step and to additionally charge the negative pressure cavity with the negative pressure via the second negative pressure interface subsequently.

12. The ophthalmologic system of claim 11, wherein the negative pressure device is configured to determine correct establishment of a negative pressure via the first negative pressure interface and to additionally charge the negative pressure cavity with the negative pressure via the second negative pressure interface in the affirmative case only.

13. A method for affixing a patient interface on a patient eye, the method comprising:
charging a negative pressure cavity of the patient interface with a negative pressure via a first negative pressure interface; and
charging the negative pressure cavity with a negative pressure via a second negative pressure interface,
wherein a first negative pressure aperture of the first negative pressure interface and a second negative pressure aperture of the second negative pressure interface are arranged in a wall of the negative pressure cavity separate from and in close vicinity to each other,
wherein the first negative pressure aperture and the second negative pressure aperture are arranged next to each other on the circumference of the negative pressure cavity,
wherein at least one of:
an angular distance between the first negative pressure aperture and the second negative pressure aperture does not exceed 30 degrees, and
a distance between the first negative pressure aperture and the second negative pressure aperture does not exceed 5 millimeters.

14. The method of claim 13, further comprising charging the negative pressure cavity with a negative pressure via the first negative pressure interface only in a first step and additionally charging the negative pressure cavity with the negative pressure via the second negative pressure interface subsequently.

15. The patient interface of claim 1, wherein the first negative pressure interface and the second negative pressure interface extend parallel to each other.

16. The patient interface of claim 15, wherein the first negative pressure interface and the second negative pressure interface are configured to be coupled to a double-lumen tube.

17. The ophthalmologic system of claim 9, wherein the first negative pressure interface and the second negative pressure interface extend parallel to each other.

18. The ophthalmologic system of claim 17, wherein the first negative pressure interface and the second negative pressure interface are configured to be coupled to a double-lumen tube.

19. The ophthalmologic system of claim 17, wherein the first negative pressure interface and the second negative pressure interface are configured to be coupled to a single lumen tube.

20. The ophthalmologic system of claim 17, wherein the negative pressure device is fluidically coupled to the negative pressure cavity via one of a single lumen tube or a double-lumen tube.

\* \* \* \* \*